United States Patent [19]

Drake

[11] Patent Number: 4,532,360

[45] Date of Patent: Jul. 30, 1985

[54] METHOD FOR PRODUCING KETONES AND PHENOLS

[75] Inventor: Charles A. Drake, Bartlesville, Okla.

[73] Assignee: Phillips Petroleum Company, Bartlesville, Okla.

[21] Appl. No.: 570,106

[22] Filed: Jan. 12, 1984

[51] Int. Cl.³ ............................................. C07C 45/33
[52] U.S. Cl. .................................... 568/357; 568/359; 568/399; 568/802
[58] Field of Search ............... 568/357, 359, 360, 802, 568/399

[56] References Cited

U.S. PATENT DOCUMENTS

| | | | |
|---|---|---|---|
| 3,349,117 | 10/1967 | Selwitz et al. | 568/802 |
| 3,437,696 | 4/1969 | Achard et al. | 260/613 |
| 3,558,687 | 1/1971 | Russell | 260/462 |
| 4,010,206 | 3/1977 | Mikami et al. | 260/586 |

*Primary Examiner*—James H. Reamer
*Attorney, Agent, or Firm*—L. M. Lavin

[57] ABSTRACT

The yield and the selectivity of an oxidation reaction of alkyl substituted benzenes to ketones and phenols in the presence of hydrogen bromide is increased through the use of cerium oxide, triphenylborate, boron phosphate and water.

14 Claims, No Drawings

METHOD FOR PRODUCING KETONES AND PHENOLS

This invention relates to the oxidation of alkyl substituted benzenes to ketones and phenols, in the presence of hydrogen bromide. It further relates to the use of additives in this reaction that increase the yield and selectivity of the reaction to ketones and phenols.

BACKGROUND OF THE INVENTION

The conventional method for producing ketones and phenols includes a first step in which a secondary alkyl substituted benzene or benzene itself is oxidized to produce a corresponding benzene hydroperoxide compound. In the second step the benzene hydroperoxide compound is acid decomposed to produce a ketone and the corresponding phenol compound. This two-step process is both complicated and slow. This led to a one-step process in which the alkyl substituted benzene is oxidized in the liquid phase by bringing oxidizing gas containing molecular oxygen into contact with the alkyl substituted benzene in the presence of hydrogen bromide and isolating the resultant ketones and corresponding phenols from the oxidation mixture.

It has been found in the instant invention that certain additives to the one-step process can give higher yields or higher selectivity or both for the ketones and the corresponding phenol compounds.

The object of this invention is a process for increasing the yield and selectivity of an alkyl substituted benzene oxidative cleavage reaction for the production of ketones and phenols. Another object of this invention is to provide catalyst systems containing additives that will increase the yield and selectivity of alkyl substituted benzene oxidative cleavage reactions for the production of ketones and phenols. Other objects will become clear from the following description.

SUMMARY OF INVENTION

According to the instant invention, an alkyl substituted benzene, preferably cyclohexylbenzene, is oxidized in one step to ketones and the corresponding phenols by the action of hydrogen bromide and optionally, hydrogen chloride in dichloroethane solvent, in the presence of one or more yield increasing and/or one or more selectivity increasing additives to optimize the production of phenols and ketones chosen from cerium oxide, triphenylborate, boron phosphate, and water.

DETAILED DESCRIPTION OF INVENTION

Any secondary alkyl substituted benzene can be used as a starting material within the scope of this invention. The secondary alkyl substituted benzenes contemplated for use in the present invention are represented by the formulas:

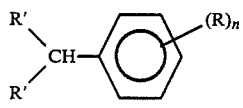 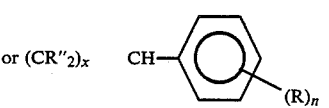

(I) (II)

wherein (R) is a $C_1-C_{20}$ alkyl, aryl, cycloalkyl, or alkaryl radical, $R'$ is independently a $C_1$ to $C_{10}$ alkyl, aryl, or alkaryl radical, $R''$ is each independently H or a $C_1$ to $C_{10}$ alkyl, aryl, or alkaryl radical, n is an integer from 0–5, and x is an integer from 2 to 11. Exemplary compounds falling under formulae (I) or (II) suitable for use in the present invention include cyclohexylbenzene, cumene, sec-butylbenzene, secpentylbenzene, and sec-hexylbenzene with cyclohexylbenzene being preferred.

The method of the present invention is effected in the presence of hydrogen bromide as a catalyst. The hydrogen bromide in the form of gas can be directly added into the oxidation mixture. The hydrogen bromide can first be dissolved in the starting material or in an organic solvent and then the solution can be mixed into the oxidation mixture. Otherwise, the hydrogen bromide can be generated by adding an inorganic bromide salt, for example sodium bromide, potassium bromide, lithium bromide, or calcium bromide; or organic acid bromide, for example, acetyl bromide, or benzoyl bromide into an oxidation mixture containing an acid, for example hydrogen chloride.

Preferably, the hydrogen bromide is present in an amount of at least 0.01 percent, more preferably 0.1 to 10 percent based on the weight of the starting alkyl substituted benzene compound in the oxidation mixture. A too large amount of the hydrogen bromide in the oxidation mixture may lead to undesirable side reactions and result in an economical disadvantage.

Hydrogen chloride is added to the oxidation mixture so that the oxidation mixture can remain acidic throughout the oxidation period. The hydrogen chloride is also cheaper and more readily available than the hydrogen bromide. The hydrogen chloride can be added in an optional amount, for example, up to supersaturation in the oxidation mixture. If the hydrogen bromide is generated from an inorganic bromide salt, for example, sodium bromide, the hydrogen chloride is preferably present in a molar ratio of at least 3:1 hydrogen chloride to sodium bromide.

A surfactant can also be added in the scope of this invention. Typical surfactants added include sodium dodecylbenzene sulfonate and benzyltriphenylphosphonium chloride. The addition of a surfactant increases the conversion of the alkyl substituted benzene and gives comparable selectivities to ketones and phenols compared to reactions without a surfactant. If a surfactant is used, a NaBr source of bromide is preferred to a LiBr source.

The alkyl substituted benzene compound can be dissolved in an organic solvent inert under the oxidation conditions of the method of the present invention, and the solution can be subjected to the oxidation process. The organic solvent can be selected from a group consisting of aromatic hydrocarbons, for example, benzene, toluene and o-,m- and p-xylenes, halogenated hydrocarbons, for example ethylene dichloride, and tetrachloromethane, and aliphatic carboxylic acids, for example, acetic acid and propionic acid. Generally the starting alkyl substituted benzene compound is dissolved in inert organic solvent from about 5 percent alkyl substituted benzene to up to solely alkyl substituted benzene.

In the method of the present invention, the oxidation is effected at a suitable temperature, preferably at a temperature of $-30°$ to $100°$ C., more preferably $0°$ to $80°$ C. Oxidation at a temperature lower than $-30°$ C. causes a low oxidation velocity. Also, oxidation at a temperature higher than $100°$ C. causes undesirable side reactions which result in a decrease in the selectivity of the resultant ketone and phenol compounds.

The amount of pressure under which the oxidation of the present invention is effected is not critical. The oxidation can be performed either under an ambient pressure, a reduced pressure, or an increased pressure as long as the oxidation can be effected in the liquid phase, and as long as the necessary amount of oxygen can be supplied into the oxidation mixture.

In the method of the present invention, the oxidizing gas can comprise oxygen gas, air or a mixture of oxygen gas and at least one inert gas, for example, nitrogen gas. The oxidizing gas usable for the method of the present invention, preferably includes therein at least 1.0 mole percent of molecular oxygen.

The yield increasing and selectivity increasing additives can be added in any amount to the oxidation mixture. Preferably they can be present in the oxidation mixture from about 0.01 weight percent to about 10 weight percent, based on the alkyl substituted benzene feedstream. Any or all of the additives may be present in the oxidation mixture. These additives are selected from cerium oxide, triphenylborate, boron phosphate, and water.

The process can be carried out either batch-wise or continuously, using a fixed catalyst bed, stirred batch reactor, a fluidized catalyst chamber, or any other suitable contacting technique.

In one example of the method of the present invention the starting alkyl substituted benzene compound or its solution in an inert organic solvent is charged to a closed vessel, for example, an autoclave. Hydrogen bromide, and if necessary, hydrogen chloride in the form of a gas or solution are charged into the closed vessel so as to be brought into intimate contact with the starting alkyl substituted benzene compound or its solution. The yield increasing and selectivity increasing additives of the instant invention are also added into the solution or mixture in the autoclave. Thereafter, an oxidizing gas is introduced into the closed vessel so that the oxidizing gas comes into contact with the starting benzene compound while the reaction mixture is stirred, shaken or agitated, and while the reaction mixture is maintained at a desired temperature and pressure.

After the completion of the oxidation reaction, the resultant phenol compound and the ketone are isolated from the reaction mixture by known methods. For example, the oxidation is neutralized by the addition of a basic solution, for example, sodium hydroxide, sodium bicarbonate, or the like solution, so as to convert the hydrogen bromide and if necessary the hydrogen chloride to nonvolatile salts. Thereafter, the neutralized mixture is subject to distillation, so as to separate the resultant ketone and phenol compounds and residual alkyl substituted benzene compound from each other.

The following specific examples using cyclohexylbenzene as the alkyl substituted benzene reactant will serve more fully to explain the practice of the present invention. However, it should be understood that these are only examples and in no way limit the present invention.

All reactions were carried out in a 300 mL Fisher-Porter bottle with all metal parts constructed of Hastelloy C. The reactor bottle was charged with reactants, sealed, then submerged in a water bath maintained at the desired reaction temperature. Once the bottle contents had equilibrated to the water bath temperature, oxygen was introduced until the vessel pressure typically reached about 150 psig. Oxygen was replenished to the reaction vessel periodically whenever the pressure dropped below about 120 psig (or whenever the pressure dropped at least 30 psig from the initial pressure).

After the desired reaction time had elapsed, the pressure was vented. Then the vessel was evacuated for about 5 minutes at 50 mm Hg to remove most of the HX, where HX represents HCl or HBr or both. Residual HX was neutralized with sodium bicarbonate, then the amount of cyclohexylbenzene, phenol and cyclohexanone was determined by gas liquid chromatography with n-pentylbenzene as the internal standard.

EXAMPLE I

Several reactions were carried out according to the teaching of U.S. Pat. No. 4,010,206. Thus, cyclohexylbenzene (CHB) in dichloroethane solvent was treated with HCl and/or HBr at 35°–40° C. for about 10–20 minutes under an initial oxygen pressure of 150 psig according to the general procedure set forth above. In all cases 0.12 moles of CHB was used. Reagents charged, reaction conditions employed and reaction results are summarized in Table I.

The results of these experiments indicate that cyclohexylbenzene conversions of up to about 28% with selectivity to cyclohexanone of less than 60% and selectivity to phenol of about 70% can be achieved according to prior art one-step oxidation processes.

EXAMPLE II

Several reactions were carried out to determine the effect of a solvent on the one-step oxidation of cyclohexylbenzene to phenol and cyclohexanone. Thus, cyclohexylbenzene was treated with HCl and NaBr in several different solvents at 150 psig initial oxygen pressure (unless noted otherwise). Reagents charged, reaction conditions employed and reaction results are summarized in Table II.

EXAMPLE III

Several reactions were carried out to investigate the effect of a water addition on the one-step oxidative cleavage of cyclohexylbenzene to give phenol and cyclohexanone. All reactions were carried out in about 60 mL of dichloroethane solvent following the general procedure set forth above. Unless otherwise noted in the table which follows, the oxygen pressure was 150 psig. Reagents charged, reaction conditions employed and reaction results are summarized in Table III.

TABLE I

| Run | Reagent, mole[a] HCl | HBr | $ClCH_2CH_2Cl$ mL | Reaction Conditions Time, min. | Temp, °C. | CHB Conv., % | % Selectivity Cyclohexanone | % Selectivity Phenol |
|---|---|---|---|---|---|---|---|---|
| 1 | 0.030 | 0.014 | 65 | 10 | 35 | 14.1 | 32.3 | 45.1 |
| 2 | 0.036 | 0.009 | 63 | 20 | 40 | 27.6 | 33.9 | 53.3 |
| 3 | 0.104 | 0.014 | 64 | 10 | 35 | 0[b] | — | — |
| 4 | 0.072 | 0.008 | 64 | 10 | 35 | 17.6 | 58.8 | 71.7 |

TABLE I-continued

| | Reagent, mole[a] | | ClCH2CH2Cl | Reaction Conditions Time, | Temp, | CHB | % Selectivity | % Selectivity |
|---|---|---|---|---|---|---|---|---|
| Run | HCl | HBr | mL | min. | °C. | Conv., % | Cyclohexanone | Phenol |
| 5 | 0.046 | 0.008 | 64 | 10 | 37 | 12.3 | 51.5 | 71.7 |
| 6 | 0 | 0.016 | 64 | 10 | 36 | 17.2 | 15.9 | 37.0 |

[a]0.12 moles of CHB used in each run
[b]When the molar ratio of acid to CHB rose to about 1, the reaction appeared to be inhibited.

TABLE II

| | | | Reagents, mole[a] | | Time, | Temp., | CHB | % Selectivity | % Selectivity |
|---|---|---|---|---|---|---|---|---|---|
| Run | Solvent | mL | HCl | NaBr | min. | °C. | Conv., % | Cyclohexanone | Phenol |
| 1 | CCl4 | 60 | 0.086 | 0.01 | 10 | 35 | 12.6 | 4.9 | 52.0 |
| 2[b] | CH2Cl2 | 60 | 0.084 | 0.01 | 30 | 35 | 17.9 | 33.1 | 54.0 |
| 3[b] | ClCH2CH2Cl | 42 | 0.11 | 0.01 | 30 | 35 | 13.8 | 50.9 | 65.6 |
| 4 | ClCl2CH2Cl | 80 | 0.078 | 0.01 | 10 | 35 | 12.4 | 73.0 | 92.4 |
| 5 | ClCH2CH2Cl | 63 | 0.088 | 0.01 | 10 | 42 | 17.2 | 66.8 | 77.1 |

[a]0.12 mole of CHB used in each run.
[b]Oxygen pressure of 100 psig employed.

TABLE III

| | Reagents, mole[a] | | | | Conditions Time, | Temp, | CHB | % Selectivity | % Selectivity |
|---|---|---|---|---|---|---|---|---|---|
| Run | HCl | NaBr | NaCl | H2O | min. | °C. | Conv., % | Cyclohexanone | Phenol |
| 1 | 0.083 | 0.01 | — | — | 30 | 25 | 21.7 | 55.3 | 71.6 |
| 2 | 0.082 | 0.002 | — | 0.028 | 30 | 25 | 24.9 | 51.0 | 67.6 |
| 3 | 0.079 | 0.01 | — | 0.029 | 30 | 25 | 37.8 | 52.9 | 77.7 |
| 4[b] | 0.083 | 0.01 | — | 0.029 | 30 | 33 | 33.1 | 52.9 | 80.3 |
| 5 | 0.084 | 0.01 | — | 0.030 | 10 | 35 | 20.0 | 56.9 | 72.0 |
| 6[b] | 0.083 | 0.01 | — | 0.056 | 30 | 35 | 35.7 | 54.2 | 81.0 |
| 7 | 0.086 | — | 0.02 | 0.028 | 30 | 25 | | No reaction | |
| 8 | 0.084 | 0.001 | 0.02 | 0.030 | 30 | 25 | 17.5 | 63.7 | 82.5 |
| 9 | 0.083 | 0.002 | 0.02 | 0.028 | 30 | 25 | 22.9 | 63.2 | 85.6 |

[a]0.12 moles of CHB used in each run
[b]Oxygen pressure of 200 psig employed

The results of these experiments demonstrate the improved results possible upon addition of small amounts of water to the one step oxidative cleavage of cyclohexylbenzene. Conversion of cyclohexylbenzene can be increased significantly as shown by runs 3 and 4; reaction time can be reduced significantly while still achieiving results comparable to the control (compare runs 1 and 5); the further addition of NaCl to the water treated system gives improved selectivities to the desired products, cyclohexanone and phenol.

EXAMPLE IV

Several reactions were carried out to investigate the effect of adding a cerium compound such as cerium oxide or cerium chloride to the one-step oxidative cleavage of cyclohexylbenzene. In addition, the effects of varying the bromide source (LiBr or NaBr) and the effect of added surfactant, such as sodium dodecylbenzenesulfonate or benzyltriphenylphosphonium chloride are also shown. Thus, cyclohexylbenzene in about 60 mL of dichloroethane was treated with HCl, LiBr or NaBr and a cerium compound, optionally in the presence of water and a surfactant. Reagents charged, reaction conditions employed and reaction results are summarized in Table IV. Unless otherwise noted in the table, all reactions were carried out at an initial oxygen pressure of 150 psig.

TABLE IV

| | Reagents, mole[e] | | | | | Time, | Temp. | CHB | % Selectivity | % Selectivity |
|---|---|---|---|---|---|---|---|---|---|---|
| Run | HCl | MBr | CeO[a] | H2O | Misc.[b] | min. | °C. | Conv., % | Cyclohexanone | Phenol |
| 1 | 0.083 | NaBr, 0.01 | — | — | — | 30 | 25 | 21.7 | 55.3 | 71.1 |
| 2[c] | 0.085 | NaBr, 0.01 | 0.13 | — | — | 30 | 25 | 28.3 | 71.9 | 87.9 |
| 3 | 0.082 | NaBr, 0.01 | 0.64 | 0.028 | — | 30 | 25 | 31.2 | 75.4 | 91.3 |
| 4 | 0.084 | NaBr, 0.01 | 0.64 | 0.014 | — | 30 | 25 | 33.0 | 63.0 | 83.1 |
| 5 | 0.082 | NaBr, 0.01 | 1.28 | 0.029 | — | 30 | 25 | 32.9 | 68.1 | 85.4 |
| 6 | 0.083 | LiBr, 0.01 | 0.64 | 0.029 | — | 30 | 25 | 44.0 | 70.8 | 89.8 |
| 7 | 0.082 | LiBr, 0.005 | 0.64 | 0.029 | — | 30 | 25 | 38.6 | 64.6 | 84.8 |
| 8 | 0.082 | LiBr, 0.01 | 1.28 | 0.028 | — | 30 | 26 | 29.3 | 71.2 | 84.4 |
| 9 | 0.084 | NaBr, 0.01 | 0.71 | 0.030 | SDB, 3.2[d] | 30 | 25 | 41.3 | 65.4 | 85.9 |
| 10 | 0.085 | NaBr, 0.01 | 0.64 | 0.028 | BTP, 2.6[d] | 30 | 25 | 38.6 | 65.3 | 86.0 |
| 11 | 0.083 | LiBr, 0.01 | 0.64 | 0.029 | BTP, 2.6[d] | 30 | 25 | 29.2 | 70.1 | 86.1 |

TABLE IV-continued

| Run | Reagents, mole[e] HCl | MBr | CeO[a] | H₂O | Misc.[b] | Time, min. | Temp. °C. | CHB Conv., % | % Selectivity Cyclohexanone | % Selectivity Phenol |
|---|---|---|---|---|---|---|---|---|---|---|
| 12[c] | 0.083 | NaBr, 0.01 | 2.0[d] | — | — | 30 | 35 | 16.7 | 58.1 | 78.1 |

[a] mmol of surfactant
[b] SDB = sodium dodecylbenzenesulfonate
BTP = benzyltriphenylphosphonium chloride
[c] Oxygen pressure of 100 psig employed
[d] CeCl₃ used instead of CeO
[e] 0.12 moles of CHB used in each run The results of these experiments demonstrate that the addition of cerium oxide to the one-step oxidative cleavage of cyclohexylbenzene gives improved feed conversion and increased selectivity to the desired products, phenol and cyclohexanone. (Compare runs 1 and 2). A further increase in conversion is obtained upon addition of water to the cerium oxide treated catalyst composition.

The source of the bromide component is shown to be relatively unimportant by comparison of runs 5 and 8. Addition of the surfactant sodium dedecylbenzenesulfonate leads to an increase in cyclohexylbenzene conversion (compare runs 4 and 9) with comparable product selectivities. Benzyltriphenylphosphonium chloride gives a similar improved feed conversion in the case of a NaBr system.

EXAMPLE V

Several reactions were carried out to investigate the effect of boron phosphate, and optionally, water, on the one-step oxidative cleavage reaction of cyclohexylbenzene. All reactions were carried out in about 60 mL of dichloroethane solvent according to the general procedure described above, at 150 psig initial oxygen pressure, unless noted otherwise in the following table. Reagents charged, reaction conditions employed and reaction results are summarized in Table V.

TABLE V

| Run | Reagents, mole[a] HCl | NaBr | BPO₄ | H₂O | Conditions Time, min. | Temp., °C. | CHB Conv., % | % Selectivity Cyclohexanone | % Selectivity Phenol |
|---|---|---|---|---|---|---|---|---|---|
| 1 | 0.083 | 0.01 | — | — | 30 | 25 | 21.7 | 55.3 | 71.1 |
| 2 | 0.084 | 0.01 | 0.001 | — | 30 | 25 | 15.0 | 68.3 | 84.0 |
| 3 | 0.082 | 0.01 | 0.001 | 0.028 | 30 | 26 | 28.6 | 68.7 | 89.1 |
| 4 | 0.084 | 0.01 | 0.002 | 0.030 | 30 | 26 | 25.0 | 68.4 | 79.7 |
| 5[b] | 0.083 | 0.01 | 0.001 | 0.029 | 30 | 26 | 43.6 | 63.1 | 83.1 |

[a] 0.12 moles of CHB was used in each run
[b] Oxygen pressure of 200 psig employed The results of these experiments demonstrate the improved product selectivities obtained upon addition of boron phosphate to the one-step oxidative cleavage reaction mixture. Comparable high selectivities with improved feed conversion are obtained upon further addition of water to the reaction mixtures. Note that a further improved conversion is obtained by increasing the oxygen pressure from 150 psig to 200 psig (compare runs 3 and 5).

EXAMPLE VI

Several reactions were carried out to determine the effect of triphenyl borate and optionally, water addition to the one-step oxidative cleavage reaction of cyclohexylbenzene. All reactions were carried out in about 60 mL of dichloroethane solvent according to the general procedure set forth above, unless otherwise indicated in the following table. Reagents charged, reaction conditions employed and reaction results are summarized in Table VI.

TABLE VI

| Run | Reagents, mole[a] HCl | NaBr | B(OPh)₃[b] | H₂O | Conditions Time, min. | Temp., °C. | CHB Conv., % | % Selectivity Cyclohexanone | % Selectivity Phenol |
|---|---|---|---|---|---|---|---|---|---|
| 1 | 0.083 | 0.01 | — | — | 30 | 25 | 21.7 | 55.3 | 71.1 |
| 2 | 0.082 | 0.01 | 3.4 | — | 30 | 25 | 21.5 | 65.0 | 87.7 |
| 3[c] | 0.083 | 0.01 | 3.4 | — | 30 | 35 | 23.5 | 53.7 | 78.6 |
| 4 | 0.082 | 0.01 | 3.4 | 0.028 | 30 | 25 | 23.7 | 67.8 | 86.1 |
| 5[c] | 0.082 | 0.01 | 3.4 | 0.029 | 30 | 35 | 31.9 | 59.0 | 83.6 |
| 6[c] | 0.083 | 0.01 | 6.9 | 0.029 | 30 | 35 | 25.5 | 58.7 | 81.9 |

[a] 0.12 moles of CHB was used in each run
[b] Expressed in mmol
[c] Oxygen pressure of 100 psig employed The results of these experiments demonstrate that improved product selectivities are achieved by adding triphenyl borate to the one-step oxidative cleavage reaction mixture. Further addition of water to the reaction mixture gives improved feed conversion as well.

I claim:

1. A method of producing ketones and phenols from alkyl, aryl, cycloalkl, and alkaryl substituted benzenes comprising contacting said substituted benzenes with an oxidizing gas containing molecular oxygen in the presence of hydrogen bromide and at least one yield increasing and selectivity increasing compound, present in a yield increasing and selectivity increasing amount, of the group consisting of boron phosphate, triphenylborate, cerium oxide and water.

2. A method according to claim 1 where said yield increasing and selectivity increasing compounds are present in an amount ranging from about 0.01 weight percent to about 10 weight percent, based on the weight of said substituted benzene.

3. A method according to claim 1 where said yield increasing and selectivity increasing compound is boron phosphate.

4. A method according to claim 1 where said yield increasing and selectivity increasing compound is triphenylborate.

5. A method according to claim 1 where said yield increasing and selectivity increasing compound is cerium oxide.

6. A method according to claim 1 where said yield increasing and selectivity increasing compound is water.

7. A method according to claim 1 where said yield increasing and selectivity increasing compounds are boron phosphate and water.

8. A method according to claim 1 where said yield increasing and selectivity increasing compounds are triphenylborate and water.

9. A method according to claim 1 where said yield increasing and selectivity increasing compounds are cerium oxide and water.

10. A method according to claim 1 where a surfactant is present.

11. A method according to claim 10 where said surfactant is chosen from sodium dodecylbenzenesulfonate and benzyltriphenylphosphonium chloride.

12. A method of producing ketones and phenols from substituted benzenes where said substituted benzenes are chosen from:

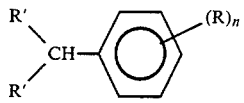 or $(CR''_2)_x$ 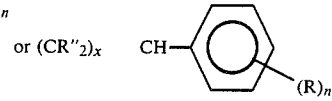

(I)       (II)

wherein (R) is a $C_1$–$C_{20}$ alkyl, aryl, cycloaklyl, or alkaryl radical, R' is independently a $C_1$ to $C_{10}$ alkyl, aryl, or alkaryl radical, R'' is each independently H or a $C_1$ to $C_{10}$ alkyl, aryl, or alkaryl radical, n is an integer from 0–5, and x is an integer from 2 to 11, comprising contacting said substituted benzenes with an oxidizing gas containing molecular oxygen in the presence of hydrogen bromide and at least one yield increasing and selectivity increasing compound, present in an amount ranging from about 0.01 weight percent to about 10 weight percent, based on the weight of said substituted benzenes, where said compounds are chosen from boron phosphate, triphenylborate, cerium oxide and water.

13. A method according to claim 12 where said substituted benzenes are chosen from cyclohexylbenzene, cumene, sec-butylbenzene, sec-pentylbenzene, and sec-hexylbenzene.

14. A method according to claim 1 where hydrogen chloride is also present.

* * * * *